(12) United States Patent
Guo et al.

(10) Patent No.: US 12,343,453 B2
(45) Date of Patent: Jul. 1, 2025

(54) DEGRADABLE REGENERATIVE MEDICAL MATERIAL FOR PROMOTING TISSUE IN-SITU REGENERATION AND PREPARATION METHOD THEREFOR

(71) Applicant: BEIJING BEST LIFE REGENERATIVE MEDICINE TECHNOLOGY CO. LTD, Beijing (CN)

(72) Inventors: Chuangzhou Guo, Beijing (CN); Fang Hu, Beijing (CN); Yuexiu Qiu, Beijing (CN); Xiaoli Yu, Beijing (CN)

(73) Assignee: BEIJING BEST LIFE REGENERATIVE MEDICINE TECHNOLOGY CO. LTD, Beijing (CN)

( * ) Notice: Subject to any disclaimer, the term of this patent is extended or adjusted under 35 U.S.C. 154(b) by 651 days.

(21) Appl. No.: 17/596,627

(22) PCT Filed: Sep. 19, 2019

(86) PCT No.: PCT/CN2019/106736
§ 371 (c)(1),
(2) Date: Dec. 15, 2021

(87) PCT Pub. No.: WO2020/252957
PCT Pub. Date: Dec. 24, 2020

(65) Prior Publication Data
US 2022/0296785 A1  Sep. 22, 2022

(30) Foreign Application Priority Data

Jun. 20, 2019 (CN) .............................. 201910538684

(51) Int. Cl.
| | |
|---|---|
| *A61L 27/54* | (2006.01) |
| *A61L 27/02* | (2006.01) |
| *A61L 27/12* | (2006.01) |
| *A61L 27/56* | (2006.01) |
| *A61L 27/58* | (2006.01) |

(52) U.S. Cl.
CPC ............. *A61L 27/54* (2013.01); *A61L 27/025* (2013.01); *A61L 27/12* (2013.01); *A61L 27/56* (2013.01); *A61L 27/58* (2013.01); *A61L 2300/412* (2013.01)

(58) Field of Classification Search
None
See application file for complete search history.

(56) References Cited

FOREIGN PATENT DOCUMENTS

| CN | 1087279 A | * | 6/1994 |
|---|---|---|---|
| CN | 1554607 A | | 12/2004 |
| CN | 101091805 A | | 12/2007 |
| CN | 103721292 A | * | 4/2014 |
| CN | 104117090 A | | 10/2014 |
| CN | 106902393 A | | 6/2017 |
| CN | 107823718 A | | 3/2018 |
| CN | 110101904 A | | 8/2019 |
| EP | 1987850 A1 | | 11/2008 |
| ES | 2378044 B2 | | 4/2012 |
| IN | 201621003266 A | | 10/2017 |
| WO | 2007017756 A2 | | 2/2007 |

OTHER PUBLICATIONS

CNIPA, Chinese Search Report issued CN Appl. No. 201910538684. 3, dated Feb. 23, 2020.
CNIPA, International Search Report issued in International App. No. PCT/CN2019/106736, dated Mar. 25, 2020.

* cited by examiner

*Primary Examiner* — H. Sarah Park
(74) *Attorney, Agent, or Firm* — LKGLOBAL | Lorenz & Kopf, LLP

(57) ABSTRACT

A degradable regenerative medical material for promoting tissue in-situ regeneration and a preparation method therefor. The degradable regenerative medicine material is formed by means of chemically bonding Si, P, O and metallic elements containing calcium, and is a regular three-dimensional net structure the material of which having a nano-scale mesoporous structure is framework, and pores and micron-scale macropores that communicate with the pores are uniformly distributed in the regular three-dimensional net structure. The preparation method for the degradable regenerative medical material comprises the steps of mixing a sol, foaming, curing and calcining. The degradable regenerative medicine material has a huge specific surface area, powerful biological activity and high biological safety, has the effect of promoting cell proliferation, may induce the rapid regeneration of its own damaged tissue cells, and achieve an in-situ tissue repair function.

8 Claims, 3 Drawing Sheets

DEGRADABLE REGENERATIVE MEDICAL MATERIAL FOR PROMOTING TISSUE IN-SITU REGENERATION AND PREPARATION METHOD THEREFOR

CROSS-REFERENCE TO RELATED APPLICATIONS

This application is a U.S. National-Stage entry under 35 U.S.C. § 371 based on International Application No. PCT/CN2019/106736, filed Sep. 19, 2019, which was published under PCT Article 21(2) and which claims priority to Chinese Application No. 201910538684.3, filed Jun. 20, 2019, which are all hereby incorporated in their entirety by reference.

FIELD OF INVENTION

The present invention relates to the technical field of biomedical materials, and specifically relates to a degradable regenerative medical material for promoting tissue in-situ regeneration and a preparation method thereof.

BACKGROUND OF THE INVENTION

Regenerative medicine is a cutting-edge cross-discipline that comprehensively applies the principles and methods of life science, material science and clinical medicine to research and develop theoretical technologies for replacing, repairing, reconstructing or regenerating various tissues and organs of the human body. It has been widely used in the treatment of congenital genetic defect diseases and various tissue and organ damages, which is a leap forward in the development of human medicine. It has become a new frontier in the field of medical biology, and has extremely important significance and value of theory and application. The development of regenerative medicine puts forward higher requirements for biomedical materials.

Biological materials refer to materials that, for medical purposes, help patients achieve rehabilitation or enhance their physical functions through diagnosis, repair, treatment, or replacement of human tissues and organs. Traditional biological materials are mainly biologically inert materials having good biocompatibility with the human body and low foreign body reaction, which makes the quality of life of patients implanted with biological materials in their bodies significantly improved within five to twenty-five years.

With the development of regenerative medicine and the accelerating rate of aging, traditional bio-inert materials can no longer meet the multiple clinical treatment needs of patients, and the focus of medical research has also changed from the original biocompatibility research to biological activity, bioremediation and regeneration research, which requires that biomaterials can be degraded so as to be completely replaced by new tissues of the human body, so that there is no obvious difference between biomaterials and the tissues of the human body itself. The regenerative medical material should have a composition and structure similar to human tissues or organs, and have good biocompatibility and inducibility. After being implanted in the human body, it can trigger the body's self-repair mechanism.

At present, the regenerative medical material used in clinical application has two main categories. One category is tissue engineering materials. The regenerative medical material of tissue engineering is implanted into the site of lesions of human tissues and organs, so that the biological materials are absorbed by the body, and at the same time, the regeneration of certain cells in the body is continuously stimulated to form new tissues and replace the cell tissues of the damaged parts, which helps the body to achieve repair and reconstruction. Tissue engineering material products have been used in some clinical treatments, such as dermatology, articular cartilage, vascular system repair and so on. The other category is in-situ tissue regeneration materials. The so-called in-situ tissue regeneration refers to the introduction of some biological materials in the form of powders, solutions or particles into the human body to release some growth factors in the form of ions, which induces the rapid regeneration of the damaged tissue cells to achieve an in-situ repair function of the original tissue. For example, the regenerative medical biomaterials are injected into the injured body, which will rebuild new bone tissue from the original bone structure.

Inorganic regenerative medical biomaterials have good biocompatibility, biological response characteristics, gene activation characteristics and the function of promoting the formation of new tissues due to their similar composition and structural characteristics of inorganic minerals in human hard tissues. It is highly valued by the biomaterials science and clinical circles, and has important applications in human tissue repair. However, the stability of the composition of inorganic regenerative medicine biomaterials makes the materials have low biological activity and slow degradation in the body, making it difficult to meet the requirements of regenerative medicine. In response to this problem, scientific researchers have done a lot of researches, including adding pore formers in the material forming process, and using inorganic regenerative medical biomaterials combined with medical polymers to form porous scaffold materials and the like to increase activity and promote degradation by increasing the contact surface between the material and body fluids. The above measures have improved the materials' performance to a certain extent, but the pore size and the uniformity of pore formation are uncontrollable during the pore-making process by adding a pore-forming agent, and the performance improvement is limited. The method of composite with polymer materials has not basically changed the structure of basic unit of material and the composite part with the polymer material blocks the contact between the materials and body fluids.

The regenerative medical materials industry has been monopolized by developed countries for a long time due to high industry barriers and high levels of intervention, which is prone to form a moat effect. At present, the medical market in China has a huge demand for the regenerative medical materials, and most of the high-end regenerative medical materials used in clinical treatment needs to be imported, which consumes a large amount of foreign exchange reserves. According to statistics, there are about 100 million patients who need regenerative medicine tissues repair and treatment every year in China. With the advent of an aging society, the demand for regenerative medicine medical devices for clinical treatment has become more prominent. In 2016, the annual sales of medical equipments used in regenerative medicine of China was about 120 billion dollars, with an annual growth rate of more than 25%. Most of them need to be directly imported or prepared from the imported regenerative medical materials. The regenerative medical materials industry in developed countries has gradually formed a monopoly situation. On the one hand, Chinese huge demand for regenerative medical devices continues to grow; on the other hand, the prices of a large number of imported products remain high due to the exclusive monopoly of the core materials for manufacturing medical devices by foreign countries, the low- and middle-income patients are unable to use high-quality regenerative medicine medical equipments, which creates a huge conflict.

In view of the problems of the existing inorganic regenerative medicine biomaterials, the inventors propose a degradable regenerative medical material with a three-dimensional network structure for promoting tissue in-situ regeneration and a preparation method thereof based on years of experiences in the design and manufacture of biomedical materials.

SUMMARY

In view of the limitations of the prior art, the main purpose of the present invention is to provide a degradable regenerative medical material for promoting tissue in-situ regeneration and a preparation method thereof. This method achieves foaming and simultaneous curing during the gelation and molding process of inorganic regenerative medicine biomaterials to form the microscopic foam body. And then the foam body is calcined at a high temperature to remove the solvent to form an inorganic regenerative medicine biomaterials with a microcosmic three-dimensional network structure, which has high foaming ratio, uniform pore size, large specific surface area, and can achieve full contact between active groups and body fluids, thereby achieving high biological activity and increasing degradation rate.

In order to achieve the above purpose, the present invention adopts the following technical solutions:

adding thickener, foam stabilizer, foaming agent, foam fixative and other additives to the mixed sol, which is composed of silicate ester, phosphate ester, and soluble metal salt, and is rich in metal element, phosphorus element and silicon element; and then mixing uniformly, heating, foaming, curing, drying and calcining to form a microscopic porous material with biological activity.

A degradable regenerative medical material for promoting tissue in-situ regeneration, the degradable regenerative medical material is formed by means of chemically bonding Si, P, O and metallic elements containing calcium, and is a regular three-dimensional net structure, a material of which having a nano-scale mesoporous structure is framework, and pores and micron-scale macropores that communicate with the pores are uniformly distributed in the regular three-dimensional net structure.

In the above-mentioned degradable regenerative medical material for promoting tissue in-situ regeneration, as a preferred embodiment, in terms of mole portions, raw materials for preparing the degradable regenerative medical material include:

40-78 portions (such as 44 portions, 46 portions, 48 portions, 50 portions, 52 portions, 54 portions, 56 portions, 58 portions, 60 portions, 62 portions, 64 portions, 66 portions, 68 portions, 70 portions, 72 portions, 74 portions, 76 portions) of silicate ester 1-17 portions (such as 8 portions, 9 portions, 10 portions, 11 portions, 12 portions, 13 portions, 14 portions, 15 portions, 16 portions) of phosphate ester 110-200 portions (such as 120 portions, 130 portions, 140 portions, 150 portions, 160 portions, 170 portions, 180 portions, 190 portions) of water 20-40 portions (such as 24 portions, 26 portions, 28 portions, 30 portions, 32 portions, 34 portions, 36 portions, 38 portions) of soluble metal salt 0.01-5 portions (such as 0.3 portions, 0.4 portions, 0.5 portions) of catalyst 1-5 portions (such as 3 portions, 4 portions, 5 portions) of alcohol solvent 0.1-5 portions (such as 0.6 portions, 0.8 portions, 1.0 portions, 1.2 portions 1.4 portions, 1.6 portions, 1.8 portions, 2.0 portions, 2.2 portions, 2.4 portions) of thickener 1-5 portions (such as 1.5 portions, 2 portions, 2.5 portions) of foam stabilizer 5-10 portions (such as 6 portions, 7 portions, 8 portions, 9 portions) of foam fixative, 1-10 portions (such as 4.5 portions, 5 portions, 5.5 portions) of foaming agent.

In the present invention, silicate ester is used as a silicon source, and its dosage should be appropriate. If its dosage is too much, the formed material system will degrade slowly, and if its dosage too little, it will not meet the requirement as carrier components.

Phosphate ester, as the phosphorus source provider of the material system, controls the degradation rate of the formed materials. Too much or too little is not conducive to degradation regulation.

The addition of too much soluble metal salt will increase the pH of the material, and the addition of too little soluble metal salt will affect the ratio of metal to phosphorus and thus affect the formation rate of hydroxyapatite.

In the above-mentioned degradable regenerative medical material, as a preferred embodiment, the silicate ester is selected at least one from the group consisting of methyl orthosilicate, ethyl orthosilicate, and propyl orthosilicate.

In the above-mentioned degradable regenerative medical material, as a preferred embodiment, the phosphate ester is selected at least one from the group consisting of phosphate monoester, phosphodiester, phosphotriester, glycerophosphate and inositol hexaphosphate.

In the above-mentioned degradable regenerative medical material, as a preferred embodiment, the soluble metal salt is selected at least one from the group consisting of inorganic salts of calcium, strontium, cuprum and zincum and alkoxides; In the above-mentioned degradable regenerative medical material, as a preferred embodiment, the water is deionized water.

In the above-mentioned degradable regenerative medical material, as a preferred embodiment, the catalyst is an acid or a base; wherein the acid is an inorganic acid or an organic acid, the inorganic acid is preferably nitric acid, hydrochloric acid or sulfuric acid, and the organic acid is preferably selected at least one from the group consisting of acetic acid, oxalic acid, maleic acid and citric acid; the base is an inorganic base or an organic amine, wherein the inorganic base is preferably selected at least one from the group consisting of sodium hydroxide, aqueous ammonia and sodium bicarbonate, and the organic amine is preferably at least one of ethylenediamine and n-propylamine.

In the above-mentioned degradable regenerative medical material, as a preferred embodiment, the alcohol solvent is at least one of methanol, ethanol, ethylene glycol, diethylene glycol and glycerol; preferably, the alcohol solvent is a mixture of at least one of methanol, ethanol, ethylene glycol and diethylene glycol with glycerol.

In the above-mentioned degradable regenerative medical material, as a preferred embodiment, the thickener is at least one of water-soluble polyvinyl alcohol, hydroxymethyl cellulose and polyethylene glycol 6000.

In the above-mentioned degradable regenerative medical material, as a preferred embodiment, the foam stabilizer is at least one of a silicon-carbon type surfactant, sodium dodecyl sulfonate, polyoxyethylene fatty acid ether, glyceryl stearate, PEG-75 stearate, ceteth-20, ceteareth-6, ceteareth-25, PEG-100 stearate, cetearyl glucoside, and sodium C20-22 alcohol phosphate.

In the above-mentioned degradable regenerative medical material, as a preferred embodiment, the foam fixative is at least one of corn protein powder, whey protein powder, starch and methyl cellulose.

In the above-mentioned degradable regenerative medical material, as a preferred embodiment, the foaming agent is a physical foaming agent, preferably, the foaming agent is one or more of pentane, hexane, heptane, petroleum ether, chlorofluoromethane, dichlorodiflulromethane, and dichlorotetrafluoroethane.

In the above-mentioned degradable regenerative medical material, as a preferred embodiment, the degradable regenerative medical material has a structure of the mesopores with a pore size of 3-10 nm, and a regular three-dimensional network structure with connected holes of a pore size of 20-100 μm (a pore size of a formed three-dimensional network structure).

In the above-mentioned degradable regenerative medical material, as a preferred embodiment, the specific surface area of the degradable regenerative medical material is 740-1500 m2/g;

In the above-mentioned degradable regenerative medical material, as a preferred embodiment, the degradable regenerative medical material has a three-dimensional network structure formed by chemical bonds of Si, P, O and metal elements, as shown by molar contents of SiO2, P2O5, and metal oxide, in the degradable regenerative medical material, $SiO_2$ content is 46.4-75.4%, P2O5 content is 3.4-9.4%, metal oxide content is 21.2-44.2%.

A method for preparing the degradable regenerative medical material for promoting tissue in-situ regeneration, comprises the steps of:

mixing a sol: add catalyst to water and stir uniformly, then add silicate ester and phosphate ester for pre-hydrolysis reaction, hydrolyze until the mixture solution becomes transparent, then add soluble metal salt, and stir until completely dissolved to obtain a mixed sol;

foaming and curing: disperse the thickener with alcohol solvent, then add to the mixed sol, stir until completely swollen and dissolved, add foam stabilizer and foam fixative, stir uniformly, then age, then add foaming agent and stir uniformly to obtain a mixture material, and then heat the mixture material for foaming and curing, and then dry cured foam to obtain a foam body; wherein thickener can not only play a role in thickening, but also help to form a film in the foaming process.

calcining: calcine the foam body until completely removing organics to obtain the degradable regenerative medical material with a three-dimensional network structure for promoting tissue in-situ regeneration.

In the preparation steps of mixing a sol, the mechanism of the pre-hydrolysis reaction is: the silicate ester and phosphate ester in the formula are hydrolyzed in the solvent system under the action of the catalyst to generate silanols and hydroxyl phosphorus monomers. Then monomers generated by hydrolysis shrink and polymerize each other into a network structure in which silicon, oxygen and phosphorus are combined by covalent bonds, and metal ions are interspersed in the network and combined with ionic bonds, so as to achieve molecular-level mixing of various elements and form the main structure composed of materials.

In the above-mentioned method for preparing the degradable regenerative medical material for promoting tissue in-situ regeneration, as a preferred embodiment, in the step of foaming and curing, aging is room temperature aging, preferably, the aging refers to aging until a viscosity reaches 6000-20000 cp (such as 7000, 8000, 9000, 10000, 11000, 12000, 13000, 14000, 15000, 16000, 17000, 18000, 19000 cp). If the viscosity is too low, it is easy to break foam during the foaming process, resulting in the escape of low boiling point physical foaming agent; if the viscosity is too high, the foaming will be difficult and the foaming ratio will be too small. Then, the temperature will be lowered to below 25° C. (because the foaming agent is the low boiling point substance, when the foaming agent is added, the temperature of the system is kept below 25° C. to prevent the foaming agent from vaporizing directly). Preferably, a stirring speed is 120-300 r/min (such as 130, 150, 170, 200, 220, 150, 270, 290 r/min) after adding the foaming agent. Preferably, the heating temperature for foaming and curing is 60-100° C. (65, 70, 75° C., 80° C., 85° C., 90° C., 95° C.), and the time is 0.5-1 h (because the boiling point of the foaming agent is 36-50° C., if the foaming and curing temperature is too low, the foaming agent cannot vaporize to foam, if the temperature is too high, the foaming agent will expand rapidly and destroy the foam-pore structure; if the curing time is too little, the foaming is incomplete, if the curing time is too large, the foaming agent will gather and cause the foam-pore to be too large). Preferably, the heating for foaming and curing is performed in a vessel with a volume five times larger than the volume of the mixture material. Preferably, drying temperature is 100-200° C., and drying until system moisture is not more than 5%.

In the above-mentioned method for preparing the degradable regenerative medical material for promoting tissue in-situ regeneration, as a preferred embodiment, in the step of calcinating, calcinating temperature is 500-1000° C. (such as 520, 540, 560, 580, 600, 620, 640, 660, 680, 700, 720, 740, 760, 800, 850, 900, 960° C.), and calcinating time is 1-3 h (such as 1.5, 2.0, 2.5 h). If the calcinating temperature is too high, it will lead to partial melting of the material and affects the microstructure. If the calcinating temperature is too low, the organics cannot be completely removed, resulting in impurity residues; too little calcination time will cause incomplete calcination, and too large calcination time is meaningless (wasting time and energy).

Compared with the prior art, the present invention has the following positive effects.

1. The present invention is simple and feasible. In the sol-gel formation process, foaming, foam-fixing and uniform pore formation can be achieved by adding foaming additives, foam stabilizing additives, etc., and the formed material has a mesoporous structure of 3-10 nm and a regular three-dimensional network structure with connected holes of 20-100 μm formed by foaming, which is conducive to orderly climbing of cells.

2. The regenerative medical material of the present invention has a huge specific surface area and powerful biological activity, and can form carbonated hydroxyapatite within 4 hours.

3. The pH of the regenerative medical material of the present invention is stable and controllable, wherein the pH of the material can be controlled between 7.4 and 10.0. The material has high biological safety and the effect of promoting cell proliferation.

4. The regenerative medical material of the present invention has controllable degradation performance, which can achieve synchronization of material degradation and cell proliferation. The material degradation rate can reach about 30% in 5 days, which can induce the rapid regeneration of damaged tissues' own cells to achieve an in-situ tissue repair function.

DETAILED DESCRIPTION OF THE EMBODIMENTS

Figure 1:
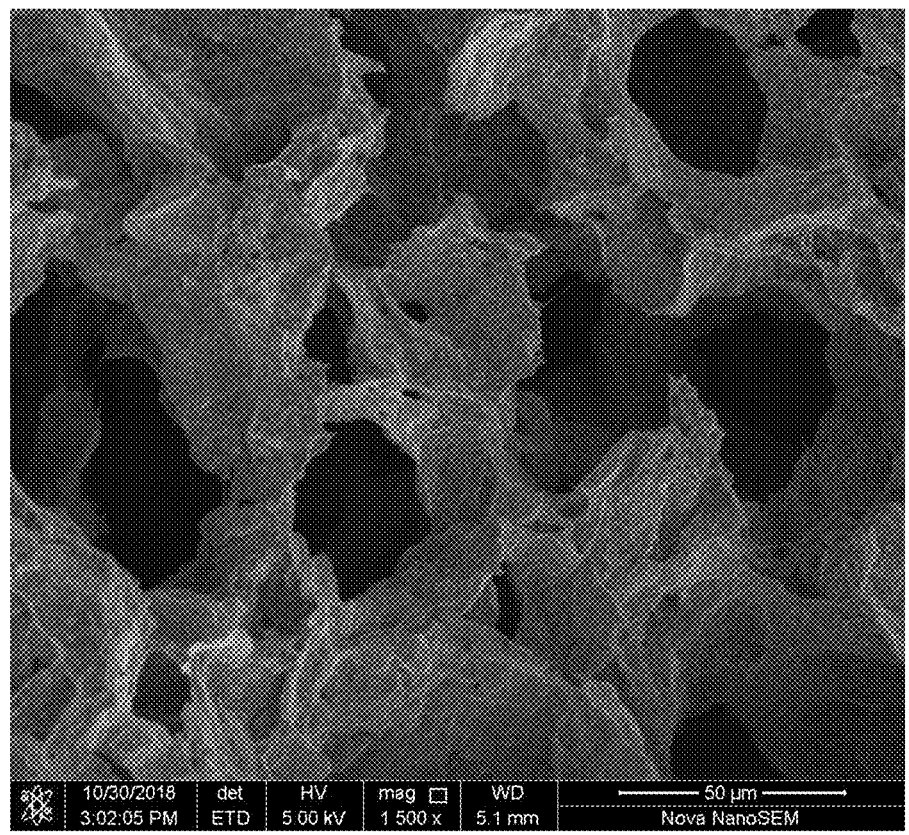
FIG. 1 is a surface topography diagram of the sample of Example 2.

In order to make the contents of the present invention easier to be understood clearly, the present invention will be further described in detail below according to the specific embodiments of the present invention. The implementation process and beneficial effects of the present invention are illustrated in detail below according to specific examples, which aims to help readers better understand the essence and characteristics of the present invention, and is not intended to limit the scope of implementation of this case.

Example 1

A degradable regenerative medical material with a three-dimensional network structure for promoting tissue in-situ regeneration, in terms of mole portions, raw materials include:
  78 portions of silicate ester
  7 portions of phosphate esters
  110 portions of deionized water
  22 portions of soluble metal salt
  0.2 portions of catalyst
  2 portions of alcohol solvent
  0.5 portions of thickener
  1 portion of foam stabilizer
  5 portions of foam fixative
  4 portions of foaming agent A method for preparing the degradable regenerative medical material with a three-dimensional network structure for promoting tissue in-situ regeneration in this example is as follows.

Firstly, prepare a mixed sol: add 110 portions of water to the reactor, add 0.2 portions of catalysts and stir uniformly, and then add 78 portions of silicate ester and 7 portions of phosphate ester for pre-hydrolysis reaction, hydrolyze until the mixture solution becomes transparent and clear, add 22 portions of soluble metal salt and stir until completely dissolved to obtain a mixed sol;

Then, disperse 0.5 portions of thickener with 2 portions of alcohol solvent and add it to the mixed sol, stir until it is completely swollen and dissolved, then add 1 portion of foam stabilizer and 5 portions of foam fixative, stir uniformly and then age at room temperature;
  continue aging until the viscosity of the system reaches 10000 cp and then cool to below 25° C., then add 4 portions of foaming agent and stir uniformly with high speed, then pour the mixture material into a vessel with a volume five times larger than the volume of the mixture material, and place it in a oven of 70° C. to heat for foaming and curing for 0.5 h;
  then, move the cured and molded foam body to an oven of 120° C. and continue to dry until the system moisture volatilizes to no more than 5%;
  place the dried foam body in a muffle furnace and calcinate at 800° C. for 1 hour to completely remove organics, the resulting material is the final product.

The silicate ester is ethyl orthosilicate;
the phosphate ester is glycerophosphate;
the soluble metal salt is a mixture of calcium chloride, zinc lactate, and strontium chloride in a molar ratio of 100:5:2, strontium, zincum and other trace elements can promote wound repair and osteoblast proliferation, strontium, zincum and other trace elements are added to improve material performance;
the catalyst is hydrochloric acid with a mass fraction of 36%;
the alcohol solvent is a mixture of ethylene glycol and glycerin with a mass ratio of 1:1;
the compatibility of the materials in the system can be increased according to the difference in the structure of each (ethylene glycol and glycerin);
the thickener is water-soluble polyvinyl alcohol PVA1788;
the foam stabilizer is H-203 polysiloxane type surfactant (Zhongshan Dongjun Chemical);
the foam fixative is a mixture of corn protein powder and starch with a mass ratio of 1:1;
The foaming agent is a mixture of n-pentane and hexane with a mass ratio of 1:1.

The material synthesized in this example is a composite structure formed by chemical bonding of each element composed of Si, P, O, and metal elements. As shown by molar contents of $SiO_2$, $P_2O_5$ and metal oxide, the material composition is 75.4% $SiO_2$, 3.4% $P_2O_5$, 21.2% metal oxides of calcium, zincum, and strontium, respectively. The final material structure contains 3-20 nm of mesopores and 40-100 μm micron-scale macropores.

Example 2

A degradable regenerative medical material with a three-dimensional network structure for promoting tissue in-situ regeneration, in terms of mole portions, includes:
  60 portions of silicate ester
  15 portions of phosphate esters
  150 portions of deionized water
  30 portions of soluble metal salt
  0.4 portions of catalyst
  3.5 portions of alcohol solvent
  1.5 portions of thickener
  2 portions of foam stabilizer
  7.5 portions of foam fixative
  5 portions of foaming agent A method for preparing the degradable regenerative medical material with a three-dimensional network structure for promoting tissue in-situ regeneration in this example is as follows.

Firstly, prepare a mixed sol: add 150 portions of water to the reactor, add 0.4 portions of catalysts and stir uniformly, and then add 60 portions of silicate ester and 15 portions of phosphate ester for pre-hydrolysis reaction, hydrolyze until the mixture solution becomes transparent and clear, add 30 portions of soluble metal salt and stir until it is completely dissolved to obtain a mixed sol;

Then, disperse 1.5 portions of thickener with 3.5 portions of alcohol and add it to the mixed sol, stir until it is completely swollen and dissolved, then add 2 portions of foam stabilizer and 7.5 portions of foam fixative, stir uniformly and then age at room temperature;

continue aging until the viscosity of the system reaches 12000 cp and then cool to below 25° C., then add 5 portions of foaming agent and stir uniformly with high speed, then pour the mixture material into a vessel with a volume five times larger than the volume of the mixture material, and place it in an oven of 60° C. to heat for foaming and curing for 1 h;

then, move the cured and molded foam body to a oven of 120° C. and continue to dry until the system moisture volatilizes to no more than 5%;

place the dried foam body in a muffle furnace and calcinate at 700° C. for 1.5 hours to completely remove organics, the resulting material is the final product.

The silicate ester is ethyl orthosilicate;

the phosphate ester is glycerophosphate;

the soluble metal salt is a mixture of calcium acetate, zinc lactate, strontium nitrate in a molar ratio of 100:5:2, the catalyst is nitric acid with a mass fraction of 50%;

the alcohol solvent is a mixture of ethylene glycol and glycerin with a mass ratio of 1:1;

the thickener is water-soluble polyvinyl alcohol PVA1788;

the foam stabilizer is a mixture of PEG-75 stearate and H-203 polysiloxane type surfactant with a mass ratio of 1:1;

the foam fixative is a mixture of whey protein powder and methyl cellulose with a mass ratio of 1:1;

The foaming agent is a mixture of n-pentane and hexane with a mass ratio of 1:1.

The material synthesized in this example is a composite structure formed by chemical bonding of each element composed of Si, P, O, and metal elements. As shown by molar contents of $SiO_2$, $P_2O_5$ and metal oxide, the material composition is 61.5% $SiO_2$, 7.7% $P_2O_5$, 30.8% metal oxides of calcium, zincum and strontium, respectively. The final material structure contains 3-7 nm of mesopores and 30-100 μm micron-scale macropores.

Example 3

A degradable regenerative medical material with a three-dimensional network structure for promoting tissue in-situ regeneration, in terms of mole portions, includes:

60 portions of silicate ester
15 portions of phosphate esters
150 portions of deionized water
30 portions of soluble metal salt
0.4 portions of catalyst
5 portions of alcohol solvent
2.5 portions of thickener
3 portions of foam stabilizer
10 portions of foam fixative
6 portions of foaming agent A method for preparing the degradable regenerative medical material with a three-dimensional network structure for promoting tissue in-situ regeneration in this example is as follows.

Firstly, prepare a mixed sol: add 150 portions of water to the reactor, add 0.4 portions of catalysts and stir uniformly, and then add 60 portions of silicate ester and 15 portions of phosphate ester for pre-hydrolysis reaction, hydrolyze until the mixture solution becomes transparent and clear, add 30 portions of soluble metal salt and stir until it is completely dissolved to obtain a mixed sol;

Then, disperse 2.5 portions of thickener with 5 portions of alcohol and add it to the mixed sol, stir until it is completely swollen and dissolved, then add 3 portions of foam stabilizer and 10 portions of foam fixative, stir uniformly and then age at room temperature;

continue aging until the viscosity of the system reaches 14000 cp and then cool to below 25° C., then add 6 portions of foaming agent and stir uniformly with high speed, then pour the mixture material into a vessel with a volume five times larger than the volume of the mixture material, and place it in a oven of 70° C. to heat for foaming and curing for 45 min;

then, move the cured and molded foam body to a oven of 120° C. and continue to dry until the system moisture volatilizes to no more than 5%;

place the dried foam body in a muffle furnace and calcinate at 700° C. for 1.5 hours to completely remove organics, the resulting material is the final product.

The silicate ester is ethyl orthosilicate;

the phosphate ester is glycerophosphate;

the soluble metal salt is a mixture of calcium nitrate, zinc nitrate, and strontium acetate in a molar ratio of 100:5:2;

the catalyst is nitric acid with a mass fraction of 50%;

the alcohol solvent is a mixture of ethylene glycol and glycerin with a mass ratio of 1:1;

the thickener is water-soluble polyvinyl alcohol PVA1788;

the foam stabilizer is a mixture of PEG-75 stearate and H-203 polysiloxane type surfactant with a mass ratio of 1:1;

the foam fixative is a mixture of whey protein powder and starch with a mass ratio of 1:1;

The foaming agent is a mixture of n-pentane and hexane with a mass ratio of 1:1.

The material synthesized in this example is a composite structure formed by chemical bonding of each element composed of Si, P, O, and metal elements. As shown by molar contents of SiO2, P2O5 and metal oxide, the material composition is 61.5% SiO2, 7.7% P2O5, 30.8% metal oxides of calcium, zincum and strontium, respectively. The finanl material structure contains 3-7 nm of mesopores and 20-80 μm micron-scale macropores.

Example 4

A degradable regenerative medical material with a three-dimensional network structure for promoting tissue in-situ regeneration, in terms of mole portions, includes:

42 portions of silicate ester
17 portions of phosphate esters
200 portions of deionized water
40 portions of soluble metal salt
0.6 portions of catalyst
5 portions of alcohol solvent
2.5 portions of thickener
3 portions of foam stabilizer
10 portions of foam fixative
6 portions of foaming agent A method for preparing the degradable regenerative medical material with a three-dimensional network structure for promoting tissue in-situ regeneration in this example is as follows.

Firstly, prepare a mixed sol: add 200 portions of water to the reactor, add 0.6 portions of catalysts and stir uniformly, and then add 42 portions of silicate ester and 17 portions of phosphate ester for pre-hydrolysis reaction, and hydrolyze until the mixture solution becomes transparent and clear, add 40 portions of soluble metal salt and stir until it is completely dissolved to obtain a mixed sol;

Then, disperse 2.5 portions of thickener with 5 portions of alcohol and add it to the mixed sol, stir until completely swollen and dissolved, then add 3 portions of foam stabilizer and 10 portions of foam fixative, stir uniformly and then age at room temperature;

continue aging until the viscosity of the system reaches 10000 cp and then cool to below 25° C., then add 6 portions of foaming agent and stir uniformly with high speed, then pour the mixture material into a vessel with a volume five times larger than the volume of the mixture material, and place it in an oven of 65° C. to heat for foaming and curing for 45 minutes;

then, move the cured and molded foam body to a oven of 120° C. and continue to dry until the system moisture volatilizes to no more than 5%;

place the dried foam body in a muffle furnace and calcinate at 600° C. for 2 hours to completely remove organics, the resulting material is the final product.

The silicate ester is ethyl orthosilicate;

the phosphate ester is dimethyl phosphate;

the soluble metal salt is a mixture of calcium nitrate, zinc acetate, and strontium nitrate in a molar ratio of 100:5:1;

the catalyst is citric acid aqueous solution with a mass fraction of 50%;

the alcohol solvent is a mixture of ethylene glycol and glycerin with a mass ratio of 1:1;

the thickener is water-soluble polyvinyl alcohol PVA1788;

the foam stabilizer is a mixture of stearate triglyceride and sodium dodecyl sulfonate with a mass ratio of 1:1;

the foam fixative is a mixture of corn protein powder and starch with a mass ratio of 1:1;

The foaming agent is a mixture of n-pentane and hexane with a mass ratio of 1:1.

The material synthesized in this example is a composite structure formed by chemical bonding of each element composed of Si, P, O, and metal elements. As shown by molar contents of $SiO_2$, $P_2O_5$ and metal oxide, the material composition is 46.4% $SiO_2$, 9.4% $P_2O_5$, 44.2% metal oxides of calcium, zincum and strontium, respectively. The finnal material structure contains 3-7 nm of mesopores and 30-100 μm micron-scale macropores.

Performance Study:

The regenerative medical material test: in order to verify whether the present invention achieves the expected effect, the three-dimensional network structure, mesopores and macroporous structure, specific surface area, biological activity, degradation performance, etc. of the samples in each example of the present invention are tested and analyzed, details are as follows:

Test-Example 1 Test of the Three-Dimensional Network Structure of the Regenerative Medical Materials The SEM test was performed on the samples obtained in Examples 1-4, and the results showed that the samples obtained in each of the Examples all formed a regular three-dimensional network structure forms with uniform pore size and pores that communicated with each other. Among them, the SEM test result of the sample obtained in Example 2 is shown in FIG. 1. As can be seen from FIG. 1, the sample obtained in Example 2 formed a regular three-dimensional network structure with uniform pore size and pores that communicated with each other.

Test-Example 2 Analysis of Mesoporous Structure and Porosity of the Regenerative Medical Materials The gas adsorption method was used to test the samples obtained in each example. The test results of the gas adsorption method shows that while the material formed macropores, the material framework constructing macroporous has a mesoporous structure. The pore size of and porosity of mesopores of each example are as follows in Table 1.

TABLE 1

Test results of pore size and porosity of samples

| Number of samples | Test results | |
| --- | --- | --- |
|  | pore size | porosity |
| Example 1 | 3-20 nm | 0.52 cc/g |
| Example 2 | 3-7 nm | 0.44 cc/g |
| Example 3 | 3-7 nm | 0.40 cc/g |
| Example 4 | 3-7 nm | 0.33 cc/g |

Test-Example 3 Specific Surface Area Detection of the Regenerative Medical Materials Specific surface areas of the samples obtained from Examples 1-4 were tested by nitrogen adsorption method and the results are shown in Table 2.

TABLE 2

Test results of specific surface areas of samples

| Number of samples | Test result ($m^2/g$) |
| --- | --- |
| Example 1 | 1282 |
| Example 2 | 932 |
| Example 3 | 1104 |
| Example 4 | 742 |

Test-Example 4 Tests of pH Value and the Stability of the Regenerative Medical Materials:

Detection method: Scheme 1: take solid samples from Examples 1-4 and add water to prepare a mixture solution with mass fraction of 5%, soak the solid samples (standing) for 2 h, and then filter and measure the pH value of the filtrate, respectively;

Scheme 2, take three groups of solid samples and prepare the mixture solution according to the method in Scheme 1, soak for different times (1 d, 3 d, 7 d) and then filter, determine the pH value of the filtrate, respectively; Scheme 3: prepare a solution according to the method of Scheme 1, soak for 24 h, filter the solution, wash and dry the filter residue, and determine the pH value again according to the method of Scheme 1.

The Test results are shown in Table 3.

TABLE 3

Test results of pH values of samples obtained from Examples 1-4

| Number of samples | pH value | | | | |
| --- | --- | --- | --- | --- | --- |
|  | Scheme 1 | Scheme 2 | | | Scheme 3 |
|  |  | 1 d | 3 d | 7 d |  |
| Example 1 | 8.82 | 8.79 | 8.81 | 8.76 | 8.78 |
| Example 2 | 8.20 | 8.23 | 8.19 | 8.14 | 8.16 |

TABLE 3-continued

Test results of pH values of samples obtained from Examples 1-4

| Number of | | pH value | | | |
|---|---|---|---|---|---|
| | | | Scheme 2 | | |
| samples | Scheme 1 | 1 d | 3 d | 7 d | Scheme 3 |
| Example 3 | 7.48 | 7.51 | 7.50 | 7.48 | 7.46 |
| Example 4 | 9.32 | 9.26 | 9.33 | 9.24 | 9.24 |

As can be seen from the results in Table 3, the pH value of the regenerative medical material of the present invention can be adjusted according to demand. The pH value of the single sample is stable during the action process. After soaking, washing, the PH value of the material remains unchanged, indicating that the material has the ability to release ions continuously.

Test-Example 5 Biological Activity Test of the Regenerative Medical Materials

The in-vitro mineralization experiments were conducted according to YY/T 0964-2014 "Methods for Determining Deposited Hydroxyapatite" to verify the biological activity of the regenerative medical materials.

Specific implementation method: Take glass conical flask or polyethylene plastic flask as the reaction vessel. The materials were placed in the reaction vessel, and measure 200.0 mL of SBF simulated body fluid per 0.3 g powder. After mixing, place the vessel in a water bath shaker of 37° C., and oscillated the reaction vessel at an oscillation speed of 175 r/min to conduct mineralization experiment. After soaking the samples for a period of time (no more than 28 d), the soaked and mineralized samples were separated, washed with deionized water and acetone solution respectively, and dried at room temperature. The samples were tested by X-ray diffraction (XRD) and scanning electron microscopy.

Figure 2:
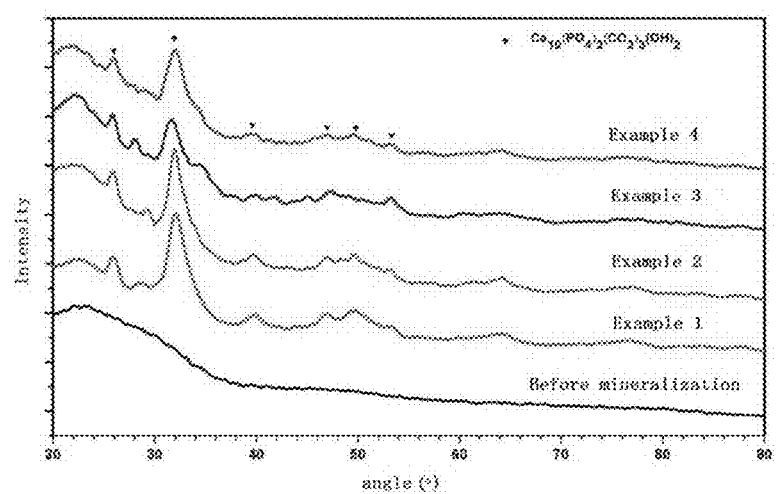
FIG. 2 is a comparison diagram of samples of Examples 1-4 before and after mineralization in the SBF simulated body fluid.
Figure 3:
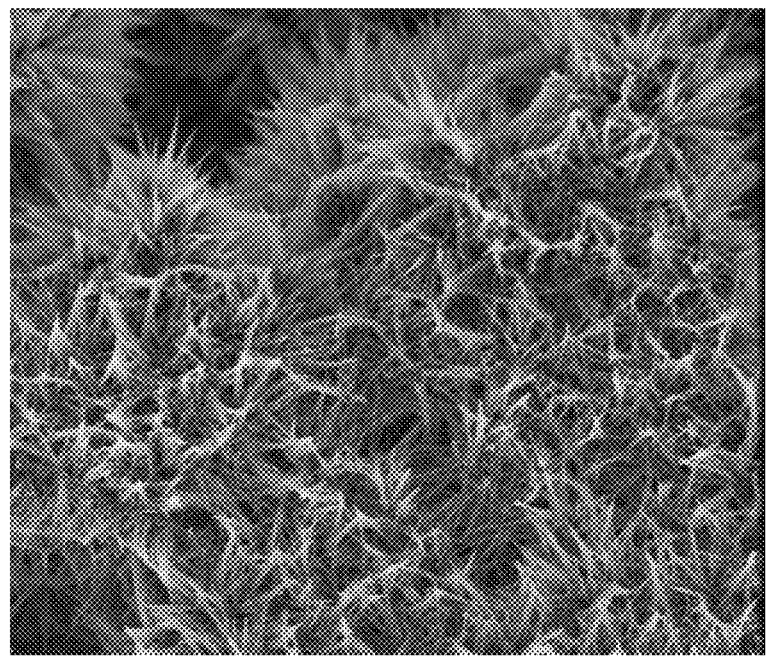
FIG. 3 is a morphology diagram of carbonated hydroxyapatite formed after the sample of Example 2 is mineralized.

In this experiment, the immersion mineralization time was 4 h, and the test results of the samples after mineralization were as follows: X-ray diffraction pattern was shown in FIG. 2 of the specification, in which obvious characteristic peaks of carbonated hydroxyapatite were formed. The results of scanning electron microscopy (SEM) were shown in FIG. 3. A three-dimensional network structure constructed by a large number of acicular and clustered carbonated hydroxyapatites was formed on the inner surface of the macropore of the material of Example 2. The rapid mineralization and formation of hydroxyapatite phase on the surface of the material indicate that the material has high biological activity and achieves the purpose of the invention.

Test-Example 6 Degradation Performance Test of the Regenerative Medical Material According to GB/T 16886.14 "Biological Evaluation of Medical Devices: Part 14", the degradation performance of the regenerative medical material was tested by the method of implant simulation solution test.

Specific Implementation Method:

TRIS buffer solution with pH of 7.4±0.1 was prepared by using tri (hydroxymethyl) aminomethane and hydrochloric acid solution (Preparation of TRIS buffer solution: put 800 ML deionized water in a 2000 ML beaker, and place the beaker on a magnetic stirrer to stir, then add 35 ML of 1 mol/L hydrochloric acid solution, and add tri (hydroxymethyl) aminomethane under the condition of stirring and adjust pH value to 7.25, finally, move the solution to a 1000 mL volumetric flask for constant volume to obtain a TRIS buffer solution); soak the material in it and oscillate for 120±1 h, and then take out the insoluble material for washing and drying, weigh and calculate the weight change before and after the test to obtain the degradation rate.

Test results are shown in Table 4.

TABLE 4

Degradation rate of the regenerative medical materials

| Number of samples | Experiment time | Degradation percentage (%) |
|---|---|---|
| Example 1 | 120 h | 19.7 |
| Example 2 | 120 h | 21.6 |
| Example 3 | 120 h | 25.2 |
| Example 4 | 120 h | 30.1 |

As can be seen from the results in Table 4, the higher the phosphorus content in the regenerative medical material, the faster the degradation rate of the material will be. When the composition is the same, the larger the specific surface area, the faster the degradation rate of the material will be.

Test-Example 7 Efficacy Verification of Regenerative Medical Materials in Animal Experiments Experimental subjects: female Guizhou miniature pigs, age: 6-10 months, weight: 20-25 kg;

Experiment period: 7+21 days (7 days for animal adaptation period and 21 days for experiment period)

Experiment methods: three defects were made on the right side of the spine of the same Guizhou pig (defect size: 5*5 cm, skin removed, fat removed, to the muscle layer, 3-6 cm deep). After adding the repair materials, and each defect was treated with traditional package technology, covering the wound, regularly changing drugs, and replacing gauze.

Defect 1: the regenerative medical material described in Example 2 of the present invention was used (denoted as Group A).

Defect 2: 45 S5 biological activity glass was used as a control group (denoted as Group B).

Defect 3: no product was used as blank control group (denoted as Group C).

Figure 4:
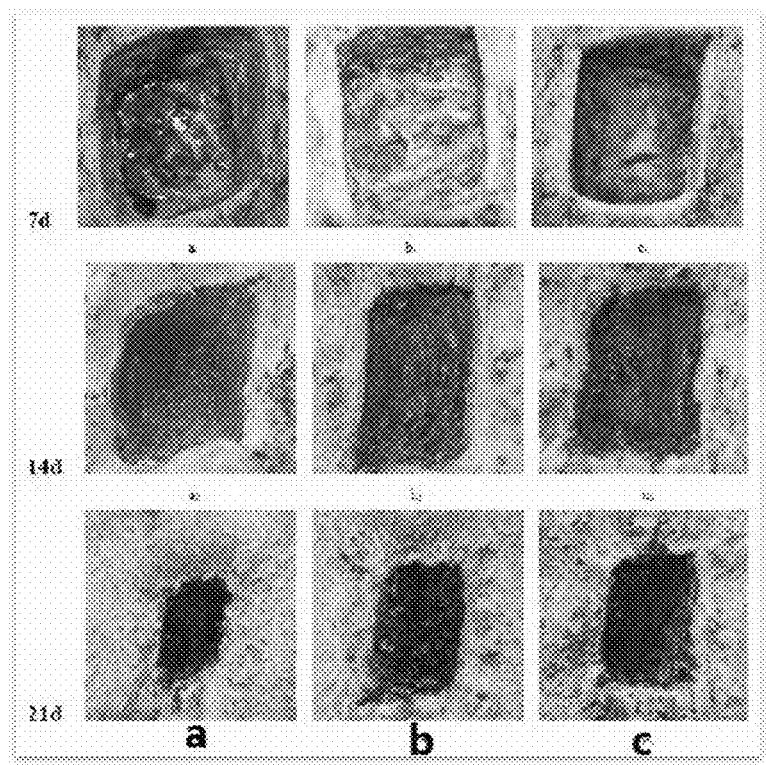
FIG. 4 is an animal experimental model and process record diagram of sample efficacy verification in Example 2 of the present invention.

The experimental model and process are shown in FIG. 4 of the specification.

Figure 5:
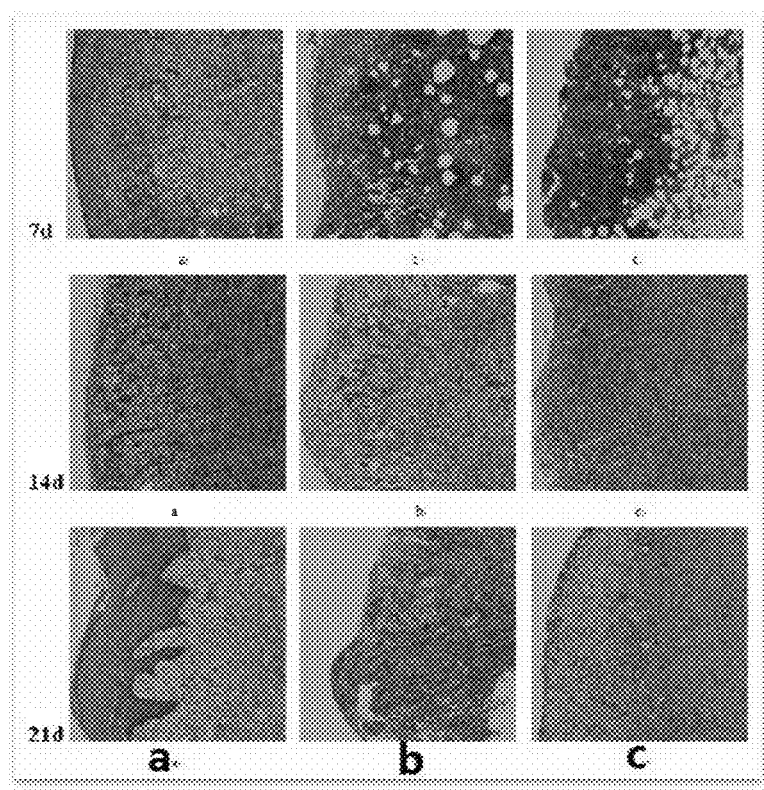
FIG. 5 is an analysis diagram of pathological slices of animal experiments of sample efficacy verification in Example 2 of the present invention.

The pathological section analysis of the experimental results is shown in FIG. 5 of the specification.

Experiment results: According to the experimental repair process (as shown in FIG. 4), the healing rate of the experimental group using the regenerative medical material of the present application in the repair process of tissue defects was significantly higher than that of the control group and the blank control group; as can be seen from the experimental pathological section analysis (FIG. 5), the experimental group using the regenerative medical material of the present application realizes orderly tissues growth, promotes the growth of capillaries, and promotes the orderly proliferation of fibroblasts, collagen tissues, etc., wherein the new tissue structure was complete, accompanied by the formation of hair follicles.

It can be seen from the above test results that the regenerative medical material synthesized by the examples of the present invention uses a material with mesoporous structure as the framework to form porous materials with a homogenous pore size and pores that communicate with each other. It has a large specific surface area, high biological activity, controllable degradation rate, and can improve the healing rate in the process of tissue repair, promote the orderly growth of tissues, and achieve in-situ tissue regeneration. It is a new type of the regenerative medical material.

Finally, it should be noted that the above examples are only used to describe the technical solutions of the present invention and do not limit them. Although the present invention is described by reference to the above-mentioned examples, those skilled in the art should understand that it is still possible to modify the technical solution recorded in the above-mentioned examples or to replace equivalents of some or all of the technical features thereof. Such modifications or replacements do not detract the nature of the corresponding technical solutions from the scope of the technical solutions in all examples of the present invention.

What is claimed is:

1. A method for preparing a degradable regenerative medical material for promoting tissue in-situ regeneration, wherein, the degradable regenerative medical material is formed by means of chemically bonding Si, P, O and metallic elements containing calcium, and is a three-dimensional network structure comprising a mesoporous structure wherein macropores that communicate with each other are uniformly distributed in the three-dimensional network structure, and in terms of mole portions, raw materials for preparing the degradable regenerative medical material include:

40-78 portions of a silicate ester;
1-17 portions of a phosphate ester;
110-200 portions of water;
20-40 portions of a soluble metal salt containing calcium;
0.01-5 portions of a catalyst;
1-5 portions of an alcohol solvent;
0.1-5 portions of a thickener;
1-5 portions of a foam stabilizer;
5-10 portions of a foam fixative; and
1-10 portions of a foaming agent;

characterized by comprising the steps of:
mixing a sol: add the catalyst to the water and stir uniformly, then add the silicate ester and the phosphate ester for pre-hydrolysis reaction, hydrolyze until the mixture solution becomes transparent, then add the soluble metal salt, and stir until completely dissolved to obtain a mixed sol;
foaming and curing: disperse the thickener with the alcohol solvent, and then add to the mixed sol, stir until completely swollen and dissolved, add the foam stabilizer and the foam fixative, stir uniformly, then age, then add the foaming agent and stir uniformly to obtain a mixture material, and then heat the mixture material for foaming and curing, and then dry cured foam to obtain a foam body; and
calcining: calcine the foam body until organics are completely removed, to obtain the degradable regenerative medical material with a three-dimensional network structure for promoting tissue in-situ regeneration, wherein,
in the step of foaming and curing, the aging is room temperature aging and refers to aging until a viscosity reaches 6000-20000 cp, and then cooling down to below 25° C.; and the speed of the stirring is 120-300 r/min after adding the foaming agent; and
in the step of foaming and curing, the temperature of the heating for foaming and curing is 60-100° C., and the time of the heating for foaming and curing is 0.5-1 h.

2. The method for preparing the degradable regenerative medical material according to claim 1, characterized in that, in the step of calcining, the temperature of the calcining is 500-1000° C., and the time of the calcining is 1-3 h.

3. The method for preparing the degradable regenerative medical material according to claim 1, characterized in that, the silicate ester is at least one selected from the group consisting of methyl orthosilicate, ethyl orthosilicate, and propyl orthosilicate; the phosphate ester is at least one selected from the group consisting of phosphate monoester, phosphodiester, phosphotriester, glycerophosphate and inositol hexaphosphate; and the soluble metal salt further comprises at least one selected from the group consisting of inorganic salts and alkoxides of calcium, strontium, cuprum and zincum.

4. The method for preparing the degradable regenerative medical material according to claim 1, characterized in that, the catalyst is an acid or a base; wherein the acid is an inorganic acid or an organic acid, wherein the inorganic acid is nitric acid, hydrochloric acid or sulfuric acid, and the organic acid is at least one selected from the group consisting of acetic acid, oxalic acid, maleic acid and citric acid; and the base is an inorganic base or an organic amine, wherein the inorganic base is at least one selected from the group consisting of sodium hydroxide, aqueous ammonia and sodium bicarbonate, and the organic amine is at least one of ethylenediamine and n-propylamine.

5. The method for preparing the degradable regenerative medical material according to claim 1, characterized in that, the alcohol solvent is at least one of methanol, ethanol, ethylene glycol, diethylene glycol and glycerol; and the thickener is at least one of water-soluble polyvinyl alcohol, hydroxymethyl cellulose and polyethylene glycol 6000.

6. The method for preparing the degradable regenerative medical material according to claim 1, characterized in that, the foam stabilizer is at least one of a silicon-carbon surfactant, sodium dodecyl sulfonate, polyoxyethylene fatty acid ether, glyceryl stearate, PEG-75 stearate, ceteth-20, ceteareth-6, ceteareth-25, PEG-100 stearate, cetearyl glucoside, and sodium C20-22 alcohol phosphate; the foam fixative is at least one of corn protein powder, whey protein powder, starch and methyl cellulose; and the foaming agent is a physical foaming agent.

7. The method for preparing the degradable regenerative medical material according to claim 5, characterized in that, the alcohol solvent is a mixture of at least two of methanol, ethanol, ethylene glycol, diethylene glycol, and glycerol.

8. The method for preparing the degradable regenerative medical material according to claim 6, characterized in that, the foaming agent is one or more of pentane, hexane, heptane, petroleum ether, chlorofluoromethane, dichlorodifluoromethane, and dichlorotetrafluoroethane.

* * * * *